(12) United States Patent
Jaunakais (10) Patent No.: US 7,491,546 B2
(45) Date of Patent: Feb. 17, 2009

(54) REAGENT DELIVERY AND PHOTOMETRIC CHLORINE ANALYSIS

(75) Inventor: Ivars Jaunakais, Rock Hill, SC (US)

(73) Assignee: Industrial Test Systems, Inc., Rock Hill, SC (US)

( * ) Notice: Subject to any disclaimer, the term of this patent is extended or adjusted under 35 U.S.C. 154(b) by 664 days.

(21) Appl. No.: 10/949,315

(22) Filed: Sep. 27, 2004

(65) Prior Publication Data

US 2006/0073603 A1    Apr. 6, 2006

(51) Int. Cl.
*G01N 33/00* (2006.01)
*G01N 31/22* (2006.01)

(52) U.S. Cl. .......................... 436/125; 422/56; 422/58; 422/82.09; 436/164; 436/169; 436/810; 435/287.7; 356/436

(58) Field of Classification Search .............. 422/82.09, 422/56–61, 102; 436/125, 169, 165, 164, 436/178, 180, 810; 435/287.9, 287.7; 356/436
See application file for complete search history.

(56) References Cited

U.S. PATENT DOCUMENTS

| | | | |
|---|---|---|---|
| 3,833,864 A | | 9/1974 | Kiess et al. |
| 3,937,613 A | | 2/1976 | Rosicky |
| 3,992,158 A | | 11/1976 | Przybylowicz et al. |
| 4,092,115 A | * | 5/1978 | Rupe et al. ................... 436/125 |
| 4,234,316 A | * | 11/1980 | Hevey ........................ 436/166 |
| 4,275,031 A | * | 6/1981 | Fischer et al. ................. 422/57 |
| 4,353,869 A | | 10/1982 | Guth |
| 4,605,629 A | | 8/1986 | Lange et al. |
| 5,155,048 A | * | 10/1992 | Williams et al. ............ 436/164 |
| 5,298,978 A | | 3/1994 | Curtis et al. |
| 5,491,094 A | * | 2/1996 | Ramana et al. ............. 436/125 |
| 5,534,441 A | | 7/1996 | Miyazaki et al. |
| 5,620,658 A | * | 4/1997 | Jaunakais ..................... 422/58 |
| 6,004,820 A | | 12/1999 | Brayton |
| 6,249,345 B1 | | 6/2001 | Kraack et al. |
| 6,413,473 B1 | * | 7/2002 | Bacon ......................... 422/56 |
| 2001/0006772 A1 | * | 7/2001 | Goldstein et al. ............. 435/2 |
| 2006/0066858 A1 | | 3/2006 | Jaunakais |

FOREIGN PATENT DOCUMENTS

EP    0 469 772 A2    2/1992

OTHER PUBLICATIONS

*Standard Methods for the Examination of Water and Wastewater*, 19th Edition, 4-43 to 4-46, 4500-Cl G (DPD Colorimetric Method), 1995.

Method #330.5: Chlorine. Total Residual (Spectrophotometric, DPD) Issued 1978.

(Continued)

*Primary Examiner*—Jill Warden
*Assistant Examiner*—Dennis M White
(74) *Attorney, Agent, or Firm*—Timothy R. Kroboth (57) ABSTRACT

Water soluble analytical agents for chlorine analysis of water are delivered into a sample from a support that is beneficially moved in the sample to assist delivery and mixing. Beneficially, an immediate photometric analysis of free chlorine is provided, and variability of measurements is reduced. Advantageously, the analysis is a touch-free chlorine analysis.

17 Claims, 2 Drawing Sheets

OTHER PUBLICATIONS

Hach, *DR/890 Colorimeter Procedures Manual*, Orientation of Sample Cells, p. 25 (1997).
Hach, *Water Analysis Handbook*, 4th Ed., Orientation of Sample Cells, Matching of Sample Cells, pp. 36-37 (2002).
Hach, *Material Safety Data Sheet* for DPD Free Chlorine Reagent, p. 1 & part of p. 2 (Mar. 26, 2003).
Hach Information for DPD Total Chlorine Reagent.
Hach, *Pocket Colorimeter II Analysis Systems Instruction Manual Chlorine*, pp. 1-13 to 1-20 (2003).
Hanna Instruments, HI 95711 *Free & Total Chlorine ISM*, Quick Reference Guide.
Palintest, *Material Safety Data Sheet* (Nov. 2002), Sections 1 & 2 only for Palintest DPD No. 1 Clear Tablets, and *Operation Instructions* sheet.
Lamotte Company, *Material Safety Data Sheet* for DPD #1 Tablet (Apr. 2004) and *1200 Colorimeter Manual*, pp. 10-11, and *Chlorine Test Procedure* sheet.

* cited by examiner fig. 6.

REAGENT DELIVERY AND PHOTOMETRIC CHLORINE ANALYSIS

FIELD OF THE INVENTION

This invention relates to photometric chlorine analysis.

BACKGROUND OF THE INVENTION

Chlorine analysis has wide commercial applicability, and is useful for testing drinking water, pool and spa water, aquarium water, industrial and environmental water, and for other types of water testing. Medical applicability includes testing of equipment such as dialysis equipment to confirm removal of chlorine and chloramine contaminants. Chlorine can be present in water as free available chlorine and as combined available chlorine. Both forms can be determined together as total available chlorine. Combined available chlorine exists as monochloramine, dichloramine and other chloro derivatives. If monochloramine is present in a sample, its interference with free chlorine analysis is dependent on sample temperature, relative concentration of monochloramine to free chlorine, and the time required to perform the analysis.

Quantitative methods for chlorine analysis that rely upon the evaluation of sample color are described in *Standard Methods for the Examination of Water and Wastewater*, 19$^{th}$ Edition, 1995 (4500-Cl), and include a DPD calorimetric method. According to the DPD colorimetric method (4500-Cl G) for free chlorine, 0.5 ml of a phosphate buffer solution and 0.5 ml of a DPD indicator solution are added to a photometer cell, 10 ml of a sample is added to the photometer cell and mixed to provide the sample with an appropriate pH and promote the color reaction, and the sample color is read immediately using appropriate photometric equipment. An immediate reading is desirable for free chlorine because of monochloramine interference and color complex degradation, which are reduced or avoided by taking the reading within one minute, especially within 30 to 45 seconds, of combining the sample and the analytical agents. As can be deduced, the less time to perform a free chlorine analysis, the more accurate the analysis should be.

The DPD indicator solution is prepared by dissolving an appropriate amount of DPD oxalate, DPD sulfate pentahydrate or anhydrous DPD sulfate in water containing sulfuric acid and disodium EDTA. In the case of the anhydrous sulfate, 0.5 ml of the DPD indicator solution contains 0.00055 g of the DPD salt.

For accurate results, pH control is essential to minimize interferences. Too low a pH may enhance monochloramine interference with free chlorine analysis. According to this US EPA accepted, DPD colorimetric standard method, the phosphate buffer solution is prepared using an about 2:1 weight ratio of potassium phosphate monobasic anhydrous to sodium phosphate dibasic anhydrous, with disodium EDTA, in an amount sufficient to provide a typical 10 ml sample with a pH in the range of about 6.2 to 6.5. The EDTA additive may advantageously overcome one or more test interferences.

For total chlorine, about 0.1 g of potassium iodide may after the free chlorine analysis, be added to the sample, and after 2 minutes, the sample color is photometrically analyzed. US EPA accepted method 330.5 for total chlorine in natural and treated waters, corresponds to the foregoing total chlorine analysis except that potassium iodide is added with the DPD indicator and phosphate buffer solutions. Method 330.5 specifies the use of DPD oxalate or sulfate, and measurement after 2 minutes.

The photometric equipment is appropriately calibrated in advance. A spectrophotometer for use at a wavelength of 515 nm and providing a 1 cm or longer light path, or a filter photometer with a wavelength measurement range of 490 to 530 nm, and a 1 cm or longer light path may be used.

In the photometric analysis art, after a BLANK reading, a photometer cell is often removed from a photometer for the addition of the analytical agents to the cell, and thereafter is re-inserted in the photometer for the actual reading. To minimize variability of measurements, a user is therefore instructed to re-insert the photometer cell so that the cell has the same orientation. Otherwise, variability in the geometry and quality of the cell glass can cause variability of measurements. Furthermore, the exterior of a photometric cell should be free of smudges or fingerprints or a water drop to ensure an accurate reading.

Commercially available, prior art technology that is based upon DPD colorimetric methodology, includes powder "pillows" (carboxylate salt, DPD salt, and sodium phosphate dibasic mixed together), and evacuated reagent ampoules with frangible tips. This prior art technology provides the analytical agents as a mixture, and specifies photometric analysis of free chlorine within one minute after combining the analytical agents and sample. For total chlorine analysis, KI reagent is also used.

Another prior art colorimetric technology for water testing in which DPD is used for chlorine analysis, is described in U.S. Pat. No. 6,004,820 to Brayton. That patented technology is based upon a closed system. As explained by Brayton, a problem with powder "pillows" is that while a "pillow" contains the precise amount of reagent needed, reagent after opening the "pillow", can be a safety hazard through hand contact or dust inhalation, or can be partially spilled with resultant possible test error.

The commercially available, prior art evacuated glass ampoules contain a pre-measured mixture of the analytical agents. In use, the ampoule tip is broken off. Contact with a broken ampoule tip can result in injury.

Other commercially available, prior art colorimetric technology is based upon crushable DPD tablets. Certain brands of these tablets include a mixture of a DPD salt and boric acid. A problem with DPD tablets, as well as with DPD powder, is that not all solids may dissolve within the specified allowed time. Moreover, incomplete solids dissolution can be expected to be worse when a sample is cold, with any cloudiness from undissolved solids potentially enhanced in the winter. As indicated, if additional time for complete solids dissolution is allowed, color complex degradation and/or monochloramine interference may result in loss of precision. Undissolved solids can lead not only to a concern about the accuracy of test results but also to lack of reproducibility. Also, DPD tablets need to be crushed, and crushing the tablets introduces an extra and time-consuming step.

As illustrated by U.S. Pat. No. 3,937,613 to Rosicky and U.S. Pat. No. 4,275,031 to Fisher et al, prior art reagent delivery devices that include a support such as an inert plastic strip or the like, and that release analytical agents for calorimetric analysis of chlorine are known. The sufficiently rigid support of such devices may be used to stir the sample, and thereafter the sample color is calorimetrically analyzed.

Rosicky teaches away from the use of DPD for chlorine analysis, for reasons of toxicity and allergenicity, and describes the combination of p-ethyl-oxyethylamino-aniline (EOAA) and non-ionic high molecular weight propyleneglycol ethyoxylates (PGE 8300 in particular) as an impregnant for filter paper fixed to a support, or as a coating on a support. The ethoxylates are described as a dispersing agent and protectant against oxidation, and as non-reactive with chlorine. Rosicky teaches a 20-40% w/v loading of PGE 8300 in an impregnating or coating solution, and visual comparison of the sample color with a color scale.

For chlorine analysis, Fisher et al (Example 6) teach the use of polyvinyl alcohol as a water soluble embedding polymer for DPD sulfate, and a waiting time of 10 minutes, instead of an immediate reading. The polyvinyl alcohol embedding polymer dissolves in the sample and releases the DPD sulfate. Thus, it appears that DPD release is retarded by the embedding polymer. In Example 6, Fischer et al disclose photometric analysis of the sample color, but do not disclose a phosphate buffer system.

Despite the foregoing advances, there continues to be a need for touch-free chlorine analysis of water that will advantageously minimize manipulations and reduce variability of measurements. Beneficially, the touch-free chlorine analysis will provide quick free chlorine analysis, thereby reducing monochloramine interference with free chorine analysis. Advantageously, the touch free-chlorine analysis will be based upon an accepted standard method for compliance testing, and in particular provide for immediate spectrophotometric analysis of free chlorine. Advantageously, there will no longer be concerns about powder spillage, or about whether adequate solids dissolution has taken place or whether undissolved solids from incomplete solids dissolution may interfere.

SUMMARY OF THE INVENTION

In accordance with the present invention, water soluble analytical agents for chlorine analysis are delivered into a sample from a support that is beneficially moved in the sample to assist delivery and mixing, and the sample color is photometrically analyzed. Advantageously, the present invention provides an undissolved solids-free sample for photometry.

Beneficially, manipulations can be minimized and variability of measurements can be reduced by taking a blank reading, by analytical agent delivery and mixing, and by photometric chlorine analysis without removal of the photometric cell from the photometric instrument. In accordance with the invention, a useful DPD salt is delivered into the sample, and accurate photometric analysis of free chlorine is achieved within one minute of, beneficially about 20 seconds after, introducing the delivery end of the support into the sample. Accordingly, the touch-free chlorine analysis of the present invention is advantageously based upon an accepted standard method for compliance testing, and in particular upon US EPA accepted standard methodology.

For pH control of the sample, the support beneficially delivers a suitable water soluble buffer system for buffering the sample to an appropriate pH. When the buffer system is a phosphate buffer system, it may be advantageous for the DPD salt and the phosphate buffer system to be physically separate from one another on the support.

For total chlorine analysis, a useful iodide salt is delivered into the sample, and after mixing and the elapse of an appropriate period of time, the sample color is photometrically analyzed for total chlorine content. If a free chlorine reading is also desired, manipulations can be minimized and variability of measurements can be reduced by the photometric cell remaining in the photometer after its insertion for a blank reading in preparation for the free chlorine reading, until its removal after the total chlorine reading.

A reagent delivery device in accordance with the present invention, includes the support, and on the support, the DPD salt. In accordance with the invention, the reagent delivery device effectively delivers the DPD salt into the sample for photometric analysis within one minute of the DPD salt-bearing portion of the device being introduced into the sample. In an advantageous embodiment, a fibrous matrix impregnated with the DPD salt, is fixed to the delivery end of the support. Alternatively, a suitable water soluble carrier that delivers the DPD salt by dissolution in the sample, may be used. Also, the DPD salt may be on the support without a carrier such as a fibrous matrix or a water soluble carrier.

It is essential to the present invention, that accurate photometric analysis of free chlorine within one minute of introducing the DPD salt-bearing portion of the device into the sample, is not in any way prevented. Thus, for DPD salt delivery to be retarded as taught by Fisher et al, would be contrary to this invention.

It can be recognized from the preceding description, that an inventive kit or apparatus beneficially includes a reagent delivery device as described, a suitable photometer cell, and appropriate photometric equipment.

In the drawing and in detailed description of the invention that follows, there are essentially shown and described only preferred embodiments of this invention, simply by way of illustration of the best mode contemplated of carrying out this invention. As will be realized, this invention is capable of other and different embodiments, and its several details are capable of modification in various respects, all without departing from the invention. Accordingly, the drawing and the detailed description are to be regarded as illustrative in nature, and not as restrictive.

BRIEF DESCRIPTION OF THE DRAWING

Reference is now made to the accompanying drawing, which forms a part of the specification of the present invention.

DETAILED DESCRIPTION OF THE INVENTION

Beneficially, the chlorine analysis of the present invention is touch-free, and analysis manipulations can be minimized and variability of measurements can be reduced. Furthermore, the present invention advantageously provides quick free chlorine analysis, thereby reducing monochloramine interference with free chorine analysis. Beneficially, the present invention is based upon a suitable DPD salt, and an immediate photometric reading of free chlorine. As a result, the touch-free chlorine analysis of the present invention, is beneficially based upon US EPA accepted standard methodology.

Advantageously, the photometry sample is free of undissolved solids from incomplete solids dissolution. As a result, user confidence replaces any concerns about whether adequate solids dissolution has taken place or whether undissolved solids may interfere with photometric accuracy.

In accordance with the touch-free chlorine analysis of the present invention, user handling of reagent powders or tablets or glass ampoules is eliminated. There are no more tablets to crush, powders to spill, glass ampoules to break, or dispensers that release irritating dust, and there is no potential for injury from broken glass ampoules. Any concern about the effect of any powder spillage or loss on precision, is removed.

Figure 1:
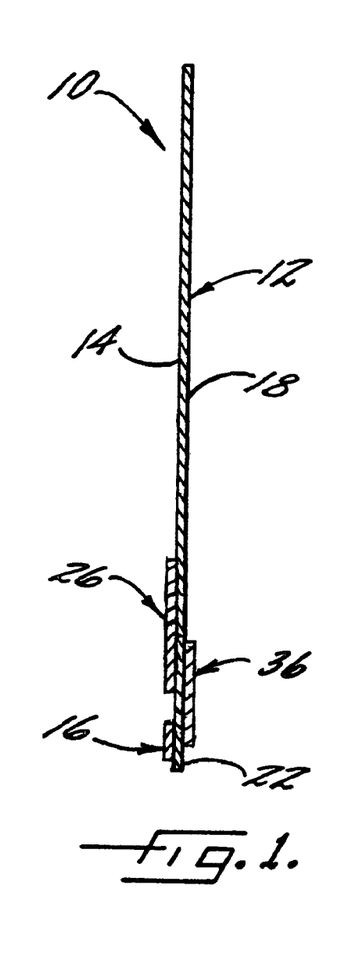
FIG. 1 is a longitudinal cross-sectional view of a preferred reagent delivery device in accordance with the present invention.
Figure 2:
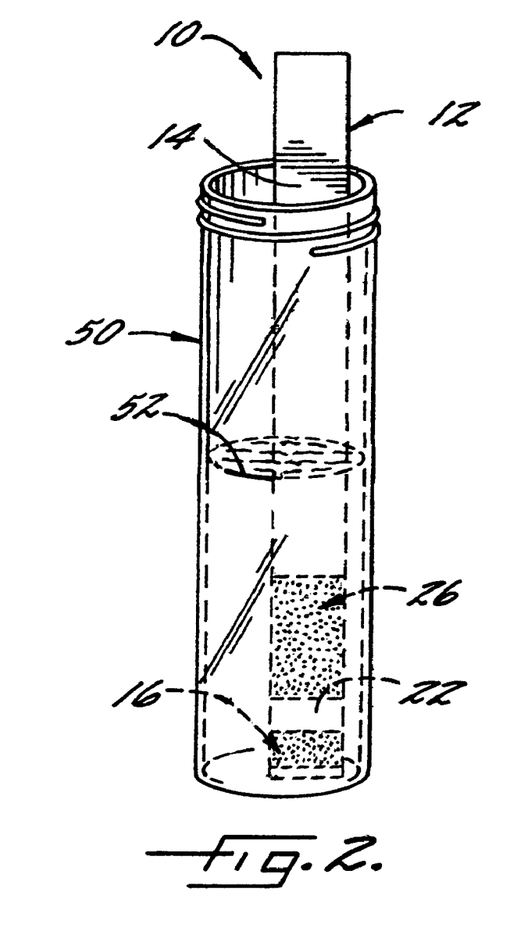
FIG. 2 is a perspective view of a photometric cell containing a sample into which the delivery end of the reagent delivery device of FIG. 1 has been introduced.

Referring to FIGS. 1 and 2 of the drawing, a preferred analytical agent delivery device 10 for photometric chlorine analysis in accordance with the present invention, is shown. Device 10 conveniently includes an elongated support or handle member 12, which is beneficially a plastic strip or other suitable support of sufficient rigidity for providing stiffness for effectively mixing the analysis sample. Typically, when a plastic strip is used, the support will range in thickness from about 0.006 to 0.020 inches. A suitable width for a plastic strip will typically range from about 4 to 12 mm or more. The thickness or width of a plastic strip may, if appropriate or desired, vary from these ranges depending upon the particular goal or goals for its application.

Any other suitable support that provides stiffness for effective sample mixing, such as a rod, in particular of square or rectangular cross-section, may be used. In any event, it will be recognized that the shape of the support is not limited to an elongated shape, although an elongated shape is advantageous for delivery and mixing.

Various inert materials may be used as the support, with preferred materials for economy being available at low cost. Suitably, the support may be made of, for example, PVC.

An analytical agent delivery device in accordance with the present invention, beneficially delivers appropriate water soluble analytical agents for chlorine analysis into an aqueous sample to be analyzed. Conveniently, to this end, disposed on a first face 14 of support 12 of device 10 is a carrier 16 for delivery of a suitable N,N-diethyl-1,4-phenylenediamine (DPD) salt, from which a carrier 26 is laterally spaced apart, and disposed on an opposite face 18 of the support is a carrier 36. Carriers 26,36 deliver a suitable water soluble buffer system into the sample to provide the sample with an appropriate pH. Conveniently, DPD carrier 16 is located near a delivery end 22 of the support, and buffer system carrier 36 may be located closer to delivery end 22 than buffer system carrier 26.

As can be recognized, a single carrier may be used in place of carriers 16,26,36 and the analytical agents accordingly combined together. However, separation of the DPD salt from a phosphate buffer system tends to increase analytical agent stability and therefore to improve test accuracy.

Conveniently, carriers 16,26,36 may be water absorbent fibrous pads that maintain structural integrity during analysis, and that are impregnated with analytical agents. Importantly, a suitable fibrous pad should be non-linting, that is, should not release fibers into the sample during the analysis procedure. Advantageously, a suitable fibrous pad is thin so as to benefit rapid analytical agent delivery, but of sufficient thickness and fiber mass to benefit loading a sufficient amount of analytical agent. Materials useful as suitable fibrous pads are known, and include cellulosic paper commercially available as a filtration material. Particularly useful filtration material for use as a fibrous pad is available from Schleicher and Schuell, and has a thickness in the range of about 0.1 to 0.6 mm. A greater pad thickness may be used, provided that enough analytical agent is delivered from the pad for immediate photometric analysis of free chlorine with accuracy.

Figure 3:
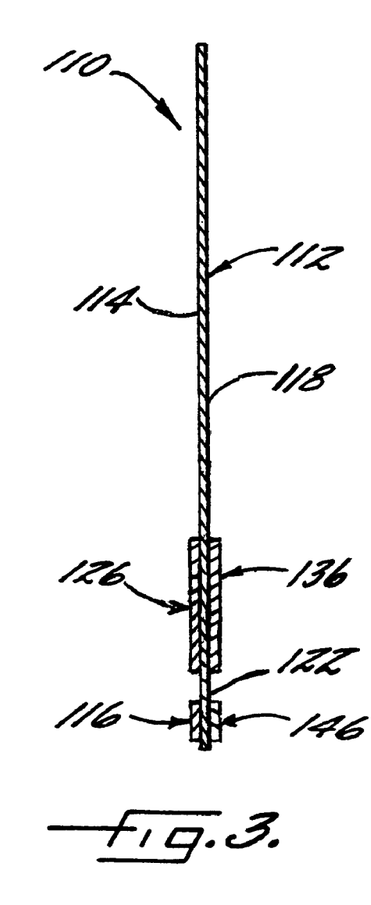
FIG. 3 is a longitudinal cross-sectional view of another preferred reagent delivery device in accordance with the present invention.

Referring now to FIG. 3, in which corresponding 100 series numbers indicate like parts, a reagent delivery device 110 in accordance with the present invention, includes an additional carrier mass 146. Carrier 146 may advantageously provide an increased loading of an analytical agent, or deliver an additional analytical agent such as KI for total chlorine analysis. Conveniently, carrier 146 may be disposed between carrier 136 and the tip of delivery end 122 of device 110.

In the case of fibrous pads, instead of using carrier 146 to increase analytical agent loading, relatively greater pad thickness can be used, but as indicated, an increase in pad thickness may reduce the speed of analytical agent delivery. Therefore, it will generally be advantageous to select fibrous pad carriers of adequate ribbon length and width to deliver an effective amount of the analytical agent of interest. It will be readily recognized that other carrier variations may be used, and that in the case of a high chlorine concentration, a sample may be diluted, in which case the dilution factor must be considered.

Referring again to FIG. 1 in particular, carriers 16,26,36 are impregnated with or otherwise carry appropriate water soluble analytical agents for chlorine analysis. In accordance with the invention, reagent delivery device 10 delivers an effective amount of a suitable water soluble DPD salt such as DPD sulfate, into the sample. The DPD salt loading of carrier 16 will vary depending upon factors including the DPD salt selected, the extent of DPD delivery within the specified allowed time, the chlorine concentration, and the sample volume. However, in any event, the loading of carrier 16 is advantageously sufficient to deliver to the sample enough DPD for accurate photometric analysis within a specified allowed time, whether testing for free chlorine or total chlorine.

If desired or appropriate, a reagent delivery device in accordance with the present invention, may be loaded with an amount of the DPD salt in excess of that used in the 4500-Cl G methodology for a 10 ml water sample. An excess loading may range from about three to ten times or more than that used in the 4500-Cl G methodology. In such case, complete delivery of the DPD salt into a sample may not be necessary for immediate photometric analysis with accuracy. For purposes of this description, by the term "immediate photometric analysis" is meant photometric analysis within one minute of introduction of the delivery end of the reagent delivery device into the sample.

Prior to or in preparation for analysis, water sample pH, alkalinity and acidity should be known or determined, and if not within the desired ranges, the sample should be appropriately adjusted. Beneficially, carriers 26,36 deliver an effective amount of a suitable water soluble, buffer system to buffer a sample to an appropriate pH to minimize or avoid interference with chlorine analysis. Generally speaking, it is desirable for the sample to be buffered to a pH of about 6.2 to 6.5. Consistent with the chemistry of the 4500-Cl G methodology, phosphate salts may be used as the buffer system, and a reagent delivery device in accordance with the present invention, may be loaded with an about 2:1 weight ratio of potassium phosphate monobasic anhydrous to sodium phosphate dibasic anhydrous in an amount sufficient, when delivered, to buffer the sample to a pH of about 6.2 to 6.5.

Fibrous pad impregnation may be accomplished in any of several ways. A suitable way is to pass a carrier material through an impregnation bath containing the particular chemicals so that the carrier becomes saturated with the impregnation solution. The carrier may be then dried at room temperature or at an elevated temperature. Advantageously, the concentration of the chemicals in an impregnation solution and the residence time of the carrier material in the solution are selected to ensure impregnation of an appropriate loading. Generally speaking, residence time will vary from about two to forty seconds, depending upon the loading desired and the carrier. If desired or appropriate, the carrier may be dipped more than once to increase the loading.

The DPD salt-impregnated fibrous pad may incorporate a water soluble barrier. A benefit is that it tends to seal the DPD salt within the fibrous pad. As a result, abrasive loss of the DPD salt from the pad may be minimized, and the barrier tends to isolate the DPD salt in the pad from any user or oxygen contact.

A mildly acidic, water soluble analytical agent may be used to form the water soluble barrier. By "mildly acidic" is meant for purposes of this description, that the barrier-forming agent has a pH in water in the range of about 3 to 5.5. A useful water soluble barrier-forming agent, as well as other analytical agents or materials used in the subject invention, cannot interfere with test accuracy by reaction with chlorine, and should not prevent immediate photometric analysis of free chlorine.

A very suitable mildly acidic, barrier-forming agent is a water soluble organic acid having a pH in water in the range of about 3 to 5, and this type of agent is not polymeric. Especially illustrative are water soluble carboxylic acids having a pH in the range of about 3 to 4, such as 2,2-bis(hydroxymethyl)propionic acid. A useful amount of the barrier-forming agent will vary depending upon the particular agent selected. When used, the water soluble barrier-forming agent may be added to the DPD salt impregnation solution in an amount ranging from about 0.5 to 10 wt. % or more, conveniently from about 1 to 5 wt. %. Caution should be exercised in that an excessive amount, may negatively impact the speed of DPD salt delivery from the fibrous pad.

Furthermore, consistent with the chemistry of 4500-Cl G methodology, EDTA disodium dihydrate may be used as a coagent, for delivery during analysis in an effective amount for overcoming one or more test interferences. If desired, about 0.08 to 1 wt. % thereof may be added to a buffer impregnation solution for fibrous pads 26,36.

In accordance with the subject invention and referring again to FIG. 3, for total chlorine analysis, carrier 146 is impregnated with or otherwise carries a suitable iodide salt, which is conveniently potassium iodide. During total chlorine analysis, reagent delivery device 110 delivers an effective amount of the iodide salt for reaction with combined available chlorine to yield iodine, which reacts with the DPD salt delivered from carrier 116.

A particularly useful coagent for the iodide salt is a polymeric agent for stabilizing the iodide salt. For this purpose, an iodide salt may be combined with an effective amount of a polyvinylpyrrolidone (PVP) for stabilizing the iodide salt. An especially useful PVP has an average molecular weight of 60,000, and is advantageously used as a mixture of 50% PVP k-60 in water with 50% methanol. Conveniently, approximately equal amounts of the iodide salt and the PVP k-60/methanol mixture may be used to impregnate carrier 146.

Conveniently, fibrous pads may be attached to the support in a variety of ways. A suitable conventional method is by use of a double-faced adhesive-material.

If appropriate or desired, carriers 16,26,36,116, 126,136, 146 may be impregnated with or otherwise carry, one or more other agents that may be of benefit for chlorine analysis. In the case of a DPD fibrous pad, exemplary agents may include butylated polyvinylpyrrolidone (commercially available as GANEX P-904 from ISP Technologies Inc), dispersing and/or wetting agents such as a polyoxyethylene-polyoxypropylene block copolymer having a wt. % of polyoxyethylene of about 80% and a molecular weight of 7680-9510 (commercially available as Lutrol® F 68 from BASF), and other wetting agents such as DOSS. A suitable amount for a DPD pad impregnation solution will vary depending upon the particular agent selected and analysis considerations, with a typical amount ranging from about 0.1 to 10 wt. %. Caution should be exercised in that an excessive amount, may negatively impact the speed of DPD salt delivery from the fibrous pad. As mentioned, the less time to perform a free chlorine analysis, the more accurate the analysis should be. If desired, the DPD fibrous matrix may include only the DPD salt.

Instead of a fibrous matrix, a carrier for an analytical agent may be a suitable water soluble material that by dissolution in the sample, delivers the analytical agent rapidly enough for immediate photometric analysis of free chlorine with accuracy, and that forms an optically clear solution. It has been found that the previously described, mildly acidic barrier-forming agent may be used as a carrier for the DPD salt. Criteria for a suitable water soluble carrier include a commercially acceptable drying time without the use of an elevated drying temperature, and preferably that the carrier is not tacky after drying. It is not necessary that a suitable water soluble carrier be mildly acidic, nor it is necessary that a suitable carrier be non-polymeric. However, it is essential that accurate photometric analysis of free chlorine within one minute of immersing the DPD salt-delivery end of the support in the sample, is not in any way prevented. Thus, retarding the release of DPD sulfate using an embedding polymer as taught by Fischer et al, is contrary to the present invention.

Figure 4:
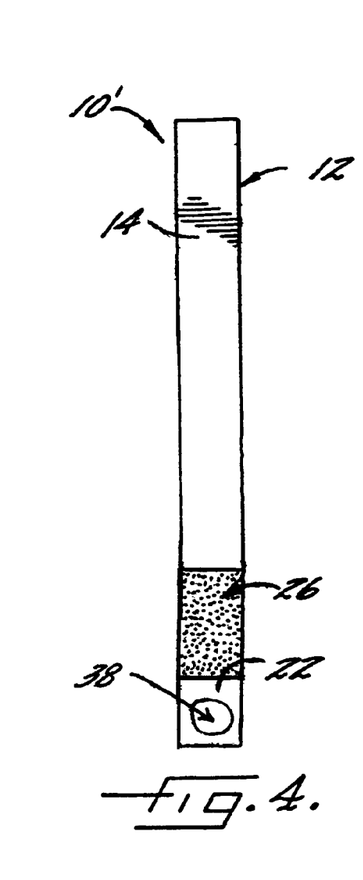
FIG. 4 is a perspective view of a variation of the reagent delivery device of FIG. 1.

As indicated, it is essential to the present invention, that the DPD salt be delivered by the reagent delivery strip into the sample for immediate photometric analysis of free chlorine with accuracy. As described, this objective may be achieved using a suitable fibrous matrix or a suitable water soluble material as a carrier for the DPD salt. Furthermore, it has been found that the foregoing inventive objective may be achieved without the use of a carrier. DPD salt may be deposited on the support, as illustrated by FIG. 4 and Example 4.

When an analytical agent is deposited on a support with a suitable water soluble material as the carrier, the relative ratio will depend upon considerations that include the desired analytical agent loading, and can be expected to vary widely. Beneficially, to obtain an excess loading of the DPD salt, the amount of the DPD salt may exceed that of the carrier, and in particular may substantially exceed the amount of the carrier. For example, a ratio (weight) of DPD salt to carrier in the range of about 4:1 to 10:1 and greater may be used. Consistent with rapid DPD salt release for immediate photometric analysis of free chlorine with accuracy, the amount of the water soluble carrier should generally be minimized, and, if desired or appropriate, referring again to FIG. 4, the carrier may be entirely omitted. Conveniently, a mixture of an analytical agent or agents and a suitable water soluble carrier is prepared in a suitable solvent system, the mixture is deposited on the support, and a drying step follows. Similarly, when a carrier is omitted for the DPD salt, a solution of the DPD salt in a suitable solvent system such as deionized water and methanol, may be deposited on the support, and a drying step follows.

As indicated, according to US EPA accepted standard methodology, a water sample size of 10 ml is used. However, other sample sizes may, if desired, be used. For example, a 25 ml sample may be used.

The time of contact of the water sample with a delivery device in accordance with the present invention, is selected to provide sufficient time for analytical agent delivery and the color reaction, using the support for mixing. Referring to reagent delivery device 10, a relatively narrower strip that carries a relatively lower loading of the DPD salt, is benefitted by a relatively longer contact time, whereas a relatively wider strip that carries a relatively higher loading of the DPD salt, requires a relatively shorter dip time. For instance, a 6 mm wide strip (6 mm wide fibrous pad 16, relatively lower loading of DPD salt) is benefitted by a contact time of 30 seconds, whereas a contact time of 10 seconds may be adequate for a 12 mm wide strip (12 mm wide fibrous pad 16, relatively higher loading of DPD salt). A highly preferred time for accurate photometric analysis of free chlorine, is about 20 seconds from the introduction of the delivery end of the reagent delivery device into a sample. A longer time can be allowed, but because of color complex degradation and monochloramine interference, a free chlorine reading should be made within one minute, and desirably within about 30 to 45 seconds.

Referring again to FIG. 2, delivery end 22 of reagent delivery device 10 is immersed in the sample, and moved within the sample to assist delivery and mixing. The delivery end may be moved within the sample in a variety of useful ways, with a back and forth movement being advantageous. A gentle rate of about two moves per second is generally preferred. After the selected time has passed, the reagent delivery device is withdrawn from the sample, and the sample color is evaluated photometrically.

Advantageously, chlorine analysis in accordance with the present invention, is useful for a wide range of sample temperatures. For instance, a very cold water sample near 0° C., can be accurately analyzed, as well as temperatures well above 25° C. Consideration must, of course, be given to higher sample temperatures increasing the tendency for chloramines to react and hence interfering with accurate free chlorine analysis, and to higher temperatures increasing color fading.

Suitable photometric cells and photometric instruments for the analysis are commercially available. Suitable photometric cells are beneficially made of glass. As previously explained, useful photometric instruments in accordance with US EPA accepted DPD colorimetric standard methodology, are a spectrophotometer for use at a wavelength of 515 nm and providing a light path of 1 cm or longer, and a filter photometer equipped with a filter having maximum transmission in the wavelength range of 490 to 530 nm and providing a light path of 1 cm or longer.

For US EPA compliance, a useful photometric instrument meets requirements for colorimeters as found in test procedures approved for the National Primary Drinking Water Regulations or National Pollutant Discharge Elimination Systems compliance monitoring programs. A US EPA accepted photometric instrument may be used with an approved test procedure such as DPD calorimetric method 4500-Cl G, without additional approval.

Figure 5:
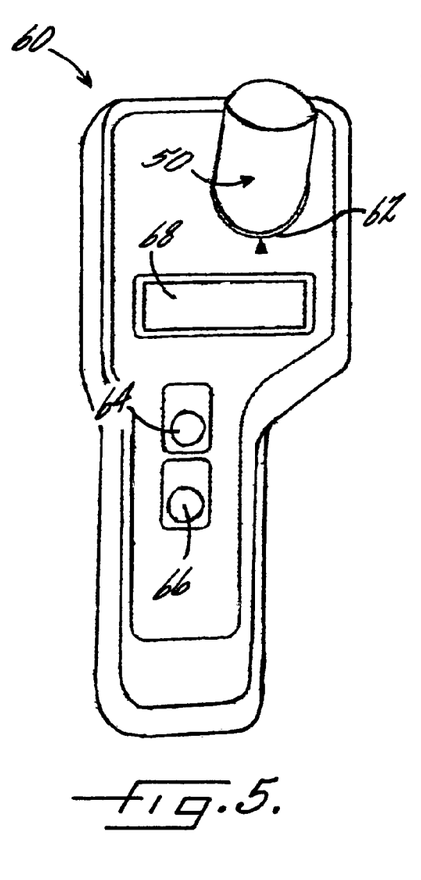
FIG. 5 is a perspective view of a useful photometric instrument, with a photometric cell inserted in the cell chamber.
Figure 6:
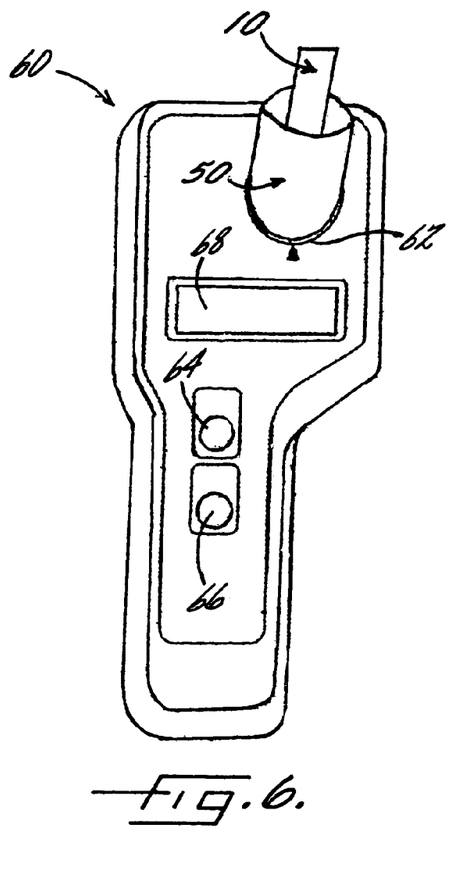
FIG. 6 is a view of the instrument of FIG. 5 with the delivery end of the reagent delivery device of FIG. 1 in the photometric cell.

Referring to FIGS. 5 and 6, an illustrative useful photometric instrument 60 includes a cell chamber 62, a power button 64, a menu button 66, and a display 68. This particular instrument is available from Palintest Ltd.

Throughout this description which includes the Examples that follow, all parts and percentages are weight percent unless otherwise specified.

EXAMPLE 1

Free Chlorine

With reference again to reagent delivery device 10 of FIGS. 1 and 2, in a convenient embodiment, support 12 is made of PVC, is 8 mm wide and has a thickness of 0.009 inches, carrier 16 is ¼" long and 8 mm wide, and carriers 26,36 are each ½" long and 8 mm wide. The carriers are fibrous pads made of Schleicher and Schuell 497 paper, which has a thickness of about 0.2 mm. ¼" long carrier 16 is loaded with approximately ten times the DPD sulfate used in the 4500-Cl G methodology, and carriers 26,36 are loaded with potassium phosphate monobasic anhydrous to sodium phosphate dibasic anhydrous in a weight ratio of 23:12. The DPD salt impregnation solution includes 3.4 wt. % of 2,2-bis(hydroxymethyl)propionic acid. The barrier benefit increases when the DPD salt is used in a high loading. The impregnation solution for buffer system carriers 26,36 includes 0.8 wt. % of EDTA disodium dihydrate.

In a preferred method of use and referring in particular to FIG. 2, 10 ml of a water sample is added to an illustrative photometric cell 50, which is provided with a marking 52 to indicate a 10 ml volume. The outside of the photometric cell is wiped to be clean and dry, and the properly dimensioned cell is inserted into a Hach Pocket Colorimeter II, and the instrument is zeroed. Thereafter, with the cell remaining in the instrument, the delivery end 22 of reagent delivery device 10, is immersed in the sample and moved back and forth for 20 seconds to deliver the analytical agents and mix the sample. The back and forth motion is at a gentle rate of about two moves per second. Immediately thereafter, delivery device 10 is withdrawn from photometric cell 50, and the sample color is photometrically read for free chlorine. A free chlorine value of 1.73 mg/L is determined.

The photometric cell is not moved or disturbed after being inserted in the photometer for zeroing the instrument. After its insertion, the cell remains in the photometer during the entire analysis procedure until its removal after the free chlorine reading.

EXAMPLE 2

Free Chlorine

In this Example, reagent delivery device 10 corresponds to that used in Example 1 except that the DPD pad impregnation solution includes 9.8 wt. % of 2,2-bis(hydroxymethyl)propionic acid. Following the method of Example 1, a free chlorine value of 1.69 mg/L is determined for the water sample.

EXAMPLE 3

Free Chlorine

In this Example, reagent delivery device 10 corresponds to that used in Example 2 except as now explained. The DPD sulfate fibrous pad is omitted, and instead, the support carries a mass 16 that is a mixture of DPD sulfate and 2,2-bis(hydroxymethyl)propionic acid. Mass 16 is prepared by depositing a small quantity of the DPD impregnation solution of Example 2 on support 12, and then drying. The loading of DPD sulfate is 0.0164 g, and the ratio of the DPD sulfate to the propionic acid is about 5:1. Following the method of Example 1, a free chlorine value of 1.82 mg/L is determined for the water sample.

EXAMPLE 4

In this Example and referring to FIG. 4, reagent delivery device 10' corresponds to reagent delivery device 10 used in Example 1 except as now explained. Fibrous pad 16 and the propionic acid are not used. Instead, support 12 carries a mass 38 of 0.0165 g DPD sulfate. Mass 38 is prepared by depositing a small quantity of a solution of 1.176 g DPD sulfate in 0.838 g deionized water and 0.40 g methanol on support 12. Device 10 is useful for chlorine analysis in accordance with the present invention.

EXAMPLE 5

Free Chlorine

In this Example, a water sample different from that of Examples 1 to 3 is used, and reagent delivery device 10 corresponds to that used in Example 1, except that the DPD pad impregnation solution includes 9.3% butylated polyvinylpyrrolidone instead of the propionic acid. Referring to FIGS. 5 and 6, a Palintest 1000 Chlorometer Duo is used as photometric instrument 60. Following the method of Example 1, a free chlorine value of 3.05 mg/L is determined.

EXAMPLE 6

Free Chlorine

In this Example, the water sample and photometric instrument used in Example 5 are used. Reagent delivery device 10 corresponds to that used in Example 1, except that the DPD pad impregnation solution lacks the propionic acid. Accordingly, carrier 16 is impregnated only with DPD sulfate. Following the method of Example 1, a free chlorine value of 3.15 mg/L is determined.

Not only are the reacted photometry samples free of undissolved solids and marked by clarity, but also blanking, analytical agent delivery and mixing, and photometric analysis are all carried out in the same photometric cell quickly and efficiently. Furthermore, for a photometer cell to remain in a photometer during an entire analysis procedure after its insertion for zeroing the instrument, until its removal after a desired reading or readings, avoids concerns about reproducibility due to variability in cell glass, or smudges or fingerprints or water drops on cells as a result of cell removal and re-insertion, or the analysis procedure.

EXAMPLE 7

Total Chlorine

Referring again to FIG. 3, in a convenient embodiment, carriers 116,126,136 of device 110 are identical to carriers 16,26,36 as described in Example 1. Additional carrier 146 is ¼" long and 8 mm wide, and is impregnated using an impregnation solution containing potassium iodide 99%, and a mixture of 50% PVP k-60 in water with 50% methanol, in a weight ratio of 13:15.

In a preferred method of use, and referring to FIG. 5, 10 ml of a water sample is added to properly dimensioned photometric cell 50, cell 50 is inserted into a Palintest 1000 Chlorometer Duo, and photometer 60 is zeroed. Thereafter, referring to FIG. 6, with cell 50 remaining in photometer 60, the delivery end 122 of reagent delivery device 110, is introduced into the sample and moved back and forth for 20 seconds to deliver the analytical agents and mix the sample. Immediately thereafter, delivery device 110 is withdrawn from the sample. Referring again to FIG. 5, after a total of three minutes from introducing its delivery end into the sample, the sample color is photometrically read for total chlorine. A total chlorine value of 1.41 mg/L is shown by display 68.

EXAMPLE 8

Free Chlorine & Total Chlorine

Reagent delivery device 10 corresponds to that used in Example 1. For free chlorine analysis and referring to FIG. 5, 10 ml of the same water sample used in Example 7 is added to photometric cell 50, and the cell is inserted into cell chamber 62 of a Palintest 1000 Chlorometer Duo, and photometer 60 is zeroed. Thereafter, referring to FIG. 6, with cell 50 remaining in photometer 60, the delivery end 22 of reagent delivery device 10, is immersed in the sample and moved back and forth for 20 seconds. Immediately thereafter, delivery device 10 is withdrawn from photometric cell 50. Referring again to FIG. 5, the sample color is immediately read for free chlorine. A free chlorine value of 0.05 mg/L is shown by display 68.

For total chlorine, a second reagent delivery device (not shown) that includes an iodide salt carrier corresponding to that of carrier 146 of device 110, is used. After the free chlorine reading, with cell 50 continuing to remain in photometer 60, the delivery end of the second reagent delivery device is introduced into the 10 ml sample and moved back and forth for 20 seconds to deliver the iodide salt and further mix the sample. Immediately thereafter, the second delivery device is withdrawn from the sample. Referring again to FIG. 5, after a total of three minutes from introducing its delivery end into the sample, the sample color is photometrically read for total chlorine. A total chlorine value of 1.44 mg/L is shown by display 68.

Beneficially, as described, photometer cell 50 remains in photometer 60 after its insertion for a blank reading in preparation for the free chlorine reading, until its removal after the total chlorine reading.

Advantageously, the inventive technology minimizes manipulations, which reduces the time and labor required for analysis, and provides an optimized blank reading, even with the cell exterior being wet or smudged. Furthermore, the inventive technology provides quick results and thereby decreases monochloramine interference. Moreover, the inventive technology assures user confidence. Beneficial applications of the technology include not only those applications outlined earlier but also applications in food processing areas.

The present invention may be carried out with various modifications without departing from the spirit or essential attributes thereof. Accordingly, reference should be made to the appended claims, rather than to the foregoing specification as indicating the scope of the invention.

The invention claimed is:

1. A touch-free colorimetric method for chlorine analysis comprising obtaining a blank reading for an aqueous sample, and then delivering into said sample an effective amount of a DPD salt from a water permeable, insoluble fibrous matrix disposed on a reagent delivery device and also providing a mixing action by moving a portion of said reagent delivery device in said sample, wherein said aqueous sample is disposed in a photometric instrument during reagent delivery, and within one minute of introducing said DPD salt into said sample, photometrically analyzing the sample color for the free chlorine in said sample, wherein said DPD salt is suitable for chlorine analysis.

2. The method of claim 1, wherein said blank reading is a zero reading.

3. The method of claim 1, wherein said sample color is photometrically analyzed about 20 seconds after said introducing.

4. The method of claim 1, further comprising delivering a suitable water soluble buffer system from at least one water permeable fibrous matrix.

5. The method of claim 4, wherein said buffer system is a phosphate buffer system, and the DPD salt fibrous matrix and said at least one fibrous matrix are disposed physically separate from one another.

6. The method of claim 5, wherein said buffer system is delivered in an effective amount to buffer said sample to a pH in the range of about 6.2 to 6.5.

7. The method of claim 1, further comprising after the free chlorine analysis, analyzing said sample for total chlorine, wherein said aqueous sample is in a photometric cell and said photometric cell remains disposed in the photometric instrument after said blank reading, until after the total chlorine reading.

8. The method of claim 1, wherein the DPD salt fibrous matrix comprises a suitable water soluble barrier.

9. The method of claim 5, wherein said phosphate buffer system is prepared using potassium phosphate monobasic anhydrous and sodium phosphate dibasic anhydrous.

10. The method of claim 1, wherein said DPD salt is DPD sulfate.

11. The method of claim 8, wherein said water soluble barrier comprises a water soluble organic acid having a pH in the range of about 3 to 5.

12. The method of claim 11, wherein said water soluble organic acid is a water soluble carboxylic acid having a pH in the range of about 3 to 4.

13. A touch-free colorimetric method for chlorine analysis comprising obtaining a blank reading for an aqueous sample, and then delivering into said sample an effective amount of a DPD salt from a water permeable, insoluble fibrous matrix disposed on a reagent delivery device and delivering an effective amount of a suitable iodide salt, and also providing a mixing action by moving a portion of said reagent delivery device in said sample, wherein said aqueous sample is disposed in a photometric instrument during reagent delivery, and photometrically analyzing the sample color for the total chlorine in said sample, wherein said DPD salt is suitable for chlorine analysis.

14. The method of claim 13, wherein said blank reading is a zero reading.

15. The method of claim 13, further comprising delivering a suitable water soluble phosphate buffer system in an effective amount to buffer said aqueous sample to a pH in the range of about 6.2 to 6.5, wherein said phosphate buffer system is delivered from at least one water permeable fibrous matrix, and the DPD salt fibrous matrix and the at least one fibrous matrix are disposed physically separate from one another.

16. The method of claim 13, wherein the DPD salt fibrous matrix comprises a suitable water soluble barrier.

17. The method of claim 16, wherein said water soluble barrier comprises a water soluble carboxylic acid having a pH in the range of about 3 to 4.

* * * * *